(12) United States Patent
Eury

(10) Patent No.: US 6,210,313 B1
(45) Date of Patent: Apr. 3, 2001

(54) RADIATION THERAPY METHOD AND DEVICE

(75) Inventor: Robert P. Eury, Cupertino, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/247,632

(22) Filed: Feb. 10, 1999

Related U.S. Application Data

(63) Continuation of application No. 08/685,447, filed on Jul. 29, 1996, now Pat. No. 5,871,436.

(51) Int. Cl.⁷ .................................................. A61N 5/00
(52) U.S. Cl. ........................... 600/3; 606/194; 424/1.11; 424/1.53
(58) Field of Search .................... 600/1–9; 606/194, 606/198; 424/1.11, 1.53; 534/10

(56) References Cited

U.S. PATENT DOCUMENTS

| | | | | |
|---|---|---|---|---|
| 4,994,560 | * | 2/1991 | Kruper, Jr. et al. | 534/10 |
| 5,002,560 | * | 3/1991 | Machold et al. | 606/198 |
| 5,034,001 | * | 7/1991 | Garrison et al. | 604/53 |
| 5,059,166 | * | 10/1991 | Fischell et al. | 600/3 |
| 5,133,956 | * | 7/1992 | Garlich et al. | 424/1.69 |
| 5,176,617 | * | 1/1993 | Fischell et al. . | |
| 5,180,368 | * | 1/1993 | Garrison . | |
| 5,199,939 | * | 4/1993 | Dake et al. | 600/3 |
| 5,213,561 | * | 5/1993 | Weinstein et al. | 600/7 |
| 5,263,963 | * | 11/1993 | Garrison et al. | 606/198 |
| 5,300,281 | * | 4/1994 | McMillan et al. | 424/1.29 |
| 5,302,168 | * | 4/1994 | Hess | 600/3 |
| 5,320,824 | * | 6/1994 | Brodack et al. | 424/1.37 |
| 5,354,257 | * | 10/1994 | Roubin et al. | 600/7 |
| 5,411,466 | * | 5/1995 | Hess | 600/3 |
| 5,456,667 | * | 10/1995 | Ham et al. | 604/107 |
| 5,484,384 | * | 1/1996 | Fearnot | 600/3 |
| 5,498,227 | * | 3/1996 | Mawad | 600/3 |
| 5,503,613 | * | 4/1996 | Weinberger | 600/3 |
| 5,503,614 | * | 4/1996 | Liprie | 600/7 |
| 5,688,486 | * | 11/1997 | Watson et al. | 424/1.65 |
| 5,730,698 | * | 3/1998 | Fischell et al. | 600/3 |

* cited by examiner

Primary Examiner—Linda C. M. Dvorak
Assistant Examiner—David M. Ruddy
(74) Attorney, Agent, or Firm—Blakely Sokoloff Taylor & Zafman LLP

(57) ABSTRACT

An implantable medical device is used to deliver a dosage of radiation to a localized site within a patient. The device is coated with a chelator selected for its bonding affinity with a specific radioisotope. A base layer and optionally a spacer layer is first applied to the device to provide a proper foundation for the chelator. Just prior to implantation, the device is immersed in a solution of the radioisotope which enables a preselected amount of such radioisotope to be adsorbed.

7 Claims, 1 Drawing Sheet

RADIATION THERAPY METHOD AND DEVICE

This application is a continuation of U.S. Ser. No. 08/685,447 filed Jul. 29, 1996, now U.S. Pat. No. 5,871,436.

BACKGROUND OF THE INVENTION

The present invention generally relates to the use of radiation therapy to treat a condition such as restenosis and more particularly pertains to the use of an implantable device to deliver a dose of radiation.

A variety of conditions have been found to be treatable by the local irradiation of tissue. In order to appropriately limit the amount of tissue that is irradiated, it is sometimes necessary to implant a small source of radiation and in order to expose the tissue to a sufficient dosage of radiation, it has been found advantageous to implant such device for an extended period of time.

Percutaneous transluminal coronary angioplasty (PTCA) is an established treatment for coronary artery disease. The procedure involves inserting a balloon catheter through the vasculature to a position where atherosclerotic plaque has collected on the vessel wall. The plaque is compressed against the vessel wall by inflating the balloon located at the distal end of the catheter in order to increase the diameter of the vessel and thereby reduce the restriction to blood flow. After sufficient expansion has been achieved, the balloon is deflated and removed, and the area of disruption begins to heal.

While this procedure is very widely used, one problem associated with PTCA is a condition known as restenosis. Restenosis is the development of further blockage in the intravascular structure, following an otherwise successful angioplasty procedure and is believed to be an exaggerated form of the normal healing process of the stretched tissue. Restenosis is thought to be caused by fibrointimal proliferation of the stretched wall in which the injured cells lining the vascular structure multiply and form fibrous tissue. Such growth at the vascular wall is an almost malignant phenomenon in which normal cells multiply at a high rate, thereby creating a new obstruction to flow through the vascular structure. It occurs in the range of approximately 15–50 percent of the cases and typically within the first six months following PTCA. Stents have been implanted in expanded vessels in an effort to maintain patency but do not appear to have much of an effect on the restenosis rate. In the event a stent has been implanted, the growth tends to occur around its ends and through any openings in its walls.

The localized irradiation of the vessel from within the vessel has been found to be effective in reducing the incidence of restenosis. Such radiation has to date been delivered via a number of different vehicles including by guide wire, balloon, temporarily implantable wire or permanently implantable stent. The delivery device is either partially or wholly formed of radioactive material or alternatively, is coated with a radioactive substance. Material giving off high levels of radiation may be briefly introduced into the body and then removed. Alternatively, material giving off a relatively lower level of radiation and with an appropriately short half-life may be introduced temporarily or alternatively left in place.

A number of shortcomings or disadvantages are associated with the prior art devices and techniques. With respect to temporarily implanted devices, implantation time is limited and therefore the radiation dose must necessarily be very high. At such high dosage rates, local radiation burns may be caused on one side of the vessel while the opposite side may receive a suboptimum dose. Moreover, due to the tendency of restenosis to occur throughout a six month period, repeated irradiation procedures would be necessary in order to adequately address the vagaries of onset.

In the case of permanently implanted devices, a compromise must be made between the shelf life of the device and its in vivo efficacious lifetime. If materials with short half-lives are used in order to reduce the long term exposure of the patient to radiation, then the shelf life of the device must necessarily be short and therefore unacceptable. If on the other hand, an isotope is used which will result in a substantial shelf life, i.e., an isotope having a long half-life, then the exposure of the patient to radiation will be long term and may be excessive. Moreover, in view of the fact that the development of restenosis typically occurs within the first six months, it has been recognized that it is desirable to limit irradiation to such time frame. Of course, attempting to substantially restrict the release of radiation from a permanently implantable device to such a limited period of time imposes further constraints on the shelf life of the device.

Another disadvantage inherent in the heretofore known delivery devices is the necessity to adequately protect all who handle the device, including the manufacturing, stocking, and shipping personnel, catheter laboratory personnel, and physicians from exposure to unreasonable radiation dosages. This requires the use of large and cumbersome containers that further complicate handling and disposal concerns. Some of the radioisotopes being considered in the industry require ion implantation into the device or transmutation of the metal in the device. The complexity of such processes greatly increases the cost of the devices.

A new approach is necessary that would overcome the shortcomings of the prior art. It would be desirable to provide a system by which a very predictable dosage of radiation can be delivered via a permanently implantable device. Moreover, it would be most desirable for such device to be producible at minimal cost, to have a substantial shelf life and present a minimal risk of exposure to radiation.

SUMMARY OF THE INVENTION

The present invention overcomes the shortcomings of the techniques and devices heretofore employed to deliver a dose of radiation to a vascular site. A method is provided for precisely controlling the dosage that is delivered to the patient while concerns relating to shelf-life of the device are obviated. Moreover, the hazards with respect to the handling of radioactive devices are substantially mitigated. Additionally, the present invention provides a method for quickly and easily rendering an implantable device radioactive. More particularly, an implantable device is prepared so as to readily adsorb a preselected amount of radioactive material and to form a sufficiently strong bond therewith so as to substantially minimize any subsequent loss thereof upon contact with bodily fluids. The present invention further provides a stent or other implantable device which facilitates the practice of such method.

These advantages are generally achieved by maintaining the implantable hardware and the radioactive material separate until just prior to implantation. By loading a precisely known quantity of material with a known half-life onto the device and immediately proceeding with the implantation procedure, a very precise dose of radiation can be delivered to the patient over a desired period of time.

The present invention provides a stent that facilitates the adsorption of a predictable amount of radioactive material thereon in the surgery room. More particularly, a stent is provided that is coated with a chelating agent. A base material and optionally, a spacer material is first coated onto the device after which the chelator is applied. This approach obviates any shelf life concerns related to the stent itself and obviates the need for special handling of the stent prior to loading. The base material is selected to both form a strong bond with the surface of the stent as well as with the spacer or chelator applied thereover. The spacer is selected to form a strong bond with the underlying base layer as well as with the chelator and serves to impart a degree of mobility to the chelator and/or to increase the number of active sites. Finally, the chelator is selected to form a strong bond with the base layer or spacer layer therebelow and of course ultimately adsorb the radioactive isotope. Such combinations of coatings are fairly tenacious, are substantially unaffected by the disinfection processes the stent is normally subjected to and have no effect on the stent's shelf life.

Just prior to implantation, the chelator-coated device is immersed in a solution containing the appropriate radioactive material to adsorb the radioisotope. The chelator- isotope combination can be chosen such that the loading is quantitative with virtually no subsequent release of the radioactive material from the implanted stent. Knowing the activity of the material along with the half-life of the radioisotope renders the total dosage of radiation that will be delivered precisely calculable. Precautions relating to the radiation must only be taken when handling the vial containing the radioactive material and when handling the stent during and after the loading step.

These and other features and advantages of the present invention will become apparent from the following detailed description of preferred embodiments which, taken in conjunction with the accompanying drawing, illustrate by way of example the principles of the invention.

DETAILED DESCRIPTION OF THE PREFERRED EMBODIMENTS

The present invention provides a system for delivering a precise dose of radiation to a vascular site via an implantable device. The device may for example be used to prevent restenosis in a blood vessel that had been subjected to an angioplastic procedure.

The device of the present invention preferably takes the form of a permanently implantable stent 10. Such stent 10 is initially provided in a collapsed state and positioned about an inflatable balloon on the distal end of a catheter. Upon maneuvering the balloon into place within the target blood vessel, the balloon is inflated which causes the stent to radially expand. Any of various mechanisms well known in the art may be incorporated in the stent in order to lock the stent into its expanded state. Subsequent deflation of the balloon and extraction of the catheter leaves the expanded stent in place to maintain the patency of the blood vessel. Further details of expandable stents and a balloon catheter delivery system are found in co-pending U.S. Ser. No. 08/454,599, filed May 31, 1995, which is incorporated herein in its entirety.

Figure 1:
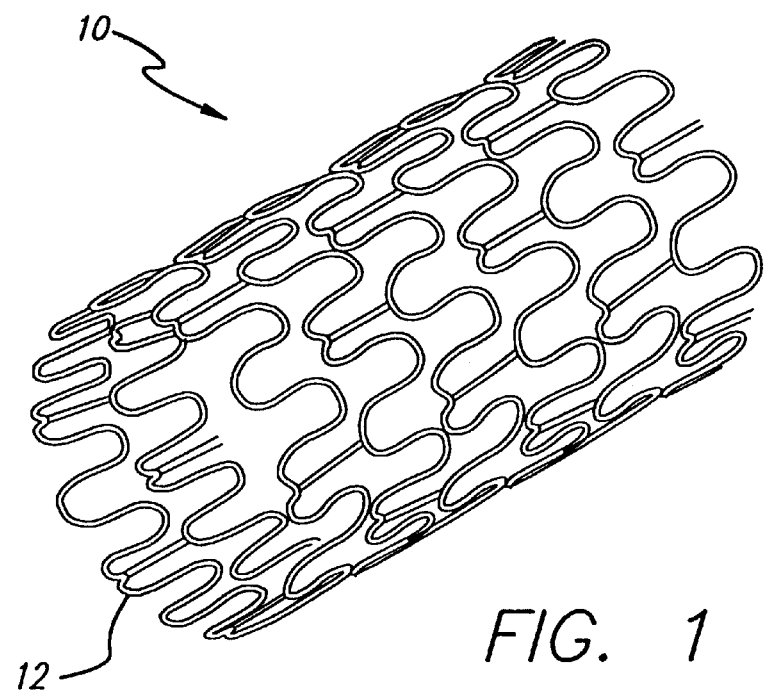
FIG. 1 is a perspective view of a typical stent having an open lattice structure and embodying features of the present invention.
Figure 2:
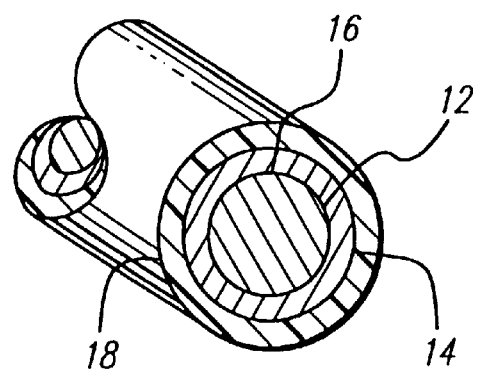
FIG. 2 is a cross-section of one wire strut of the stent of FIG. 1 depicting the various layers attached to the stent.

Such stent 10 is prepared in accordance with the present invention to deliver a preselected dose of radiation. FIGS. 1 and 2 depict stent 10 embodying features of the present invention. The exterior surface 12 of stent 10 is first selectively coated with a base layer 14 that serves as a primer or foundation. The base material is selected for its ability to adhere or bond to the surface of the stent while providing a surface to which the next layer readily bonds. An intermediate spacer layer 16 is optionally bonded to the base layer for the purpose of providing sufficient mobility to the chelating functionality that is subsequently applied thereto and/or to increase the number of active sites available to the chelating moiety thereby serving as a chemical amplifier. The chelator 18 is covalently attached to either the spacer material 16 or directly to the base layer 14. The chelator is selected to form a strong bond with the underlying material and have a strong affinity for the particular radioisotope to be used. The top layer is applied just prior to use and comprises the radioisotope that is adsorbed by the chelator. The radioisotope is selected based on the type of radiation it emits and its half-life.

The stent may be constructed of metal or a polymer. Stainless steel is the preferred material of construction.

The base layer may comprise gold or any organic coating that contains a nucleophile, or potential nucleophile. These sites could potentially be aliphatic, or benzylic carbons $\alpha$ to an ester, ketone or nitrile. Alternatively, they could be alcohols, amines, ureas or thiols. Possible base layers include polyurethane, poly (ethylene-vinyl alcohols), poly (vinyl alcohols), most hydrogels and polyarcylates.

The spacer layer is preferably attached to the base layer by nucleophilic substitution due to the degree of control afforded by such reaction. Alternatively, radical grafting processes may be employed. Possible spacer materials include $\alpha$, $\omega$-mercaptoalkylamines, diisocyanates, diacid chlorides, dialkylamines, $\alpha$, $\omega$-hydroxyalkylamines, dihydroxyalkanes (PEO) and dimercaptoalkanes.

The chelator is selected to form a covalent bond with the underlying layer, i.e., either the spacer or the base, and for a very high binding affinity for the radioisotope. Possible chelator functionalities include acetates (monocarboxylic acids), acetylacetone, benzoylacetone, citric acid, 1,2-diaminocyclohexane-N,N,N',N'-tetraacetic acid, ethlyenediamine-N,N,N',N'-tetraacetic acid, and pyridine-2,6-dicarboxylic acid.

The radioisotope is selected based on the type of emission, its half-life and the strength of its bond to the chelator which must be sufficient so as not to be displaced by ions present in the blood. The preferred isotope is a $\gamma$-emitter because $\gamma$-radiation penetrates too deeply into tissue and the energy of $\alpha$-particles is insufficient. The half-life of the radioisotope should be between 24 hours and 2 months, preferably between 2–18 days. The shorter the half-life, the more problematic the shipping and storage of the radioactive material becomes while the longer the half-life the more excessive the delivered the dosage becomes in view of the biological process currently understood to be involved in the processes of restenosis.

The most preferred combination of materials is a stainless steel stent, a gold base layer, $\alpha$, $\omega$-mercaptoalkylamine as a spacer, $N^1$-(2-hydroxethyl)-ethylenedramine - $N,N,N^1$ - triacetic acid as a chelator and $Ir^{192}$ as the radioisotope.

In the practice of the invention the stent is first prepared by applying the base layer, then optionally the spacer layer and finally the chelator. The coated stent is subsequently sterilized and processed along with the stent and associated devices. The subsequent shelf life and handling constraints are substantially dictated by the base stent and catheter rather than the coating.

The radioisotope, suspended in a solution contained in a vial, is handled separately according to the general methods with which hospitals are acquainted. Just prior to implantation, the stent is immersed in the vial in order to allow the chelator to adsorb the radioisotope. The loaded stent is subsequently maneuvered into position within the patient and expanded to be permanently left in place. The radiation emitted by stent gradually diminishes as a function of its half-life but is sufficient during the critical six month time frame to preclude or at least minimize the chance of restenosis. Radiation subsequently continues to subside to insignificant levels obviating the need to remove the device.

While a particular form of the invention has been illustrated and described, it will also be apparent to those skilled in the art that various modifications can be made without departing from the spirit and scope of the invention. More particularly, any type of implantable device may be prepared in accordance with the invention and the method may be practiced to treat any type of condition that has been found to respond to the localized irradiation of tissue. Accordingly, it is not intended that the invention be limited except by the appended claims.

What is claimed is:

1. An intravascular medical device for providing radiation treatment with a preselected amount of a preselected radioisotope adsorbed from solution, comprising:

an implantable component;

a chelating coating attached to a preselected surface of said component, said chelating coating being selected to have a binding affinity for said radioisotope; and a treatment amount of said radioisotope adsorbed by said chelating coating and substantially equal to said preselected amount loaded from solution.

2. The medical device of claim 1, wherein said implantable component comprises an expandable stent.

3. The medical device of claim 1, further comprising a base layer attached to said preselected surface of said component and disposed below said chelating coating.

4. The medical device of claim 1, wherein said preselected amount of said radioactive isotope adsorbed by said chelating coating has radioactively decayed into said treatment amount.

5. The medical device of claim 1, wherein said radioactive isotope comprises a P-emitter.

6. The medical device of claim 5, wherein said β-emitter has a half-life of between 24 hours and 2 months.

7. The medical device of claim 6, wherein said β-emitter has a half-life of between 2 and 18 days.

* * * * *